(12) United States Patent
Kawanaka

(10) Patent No.: US 8,911,753 B2
(45) Date of Patent: Dec. 16, 2014

(54) SKIN-COVERING SHEET FOR IMPREGNATION WITH COSMETIC PREPARATION AND FACE MASK

(75) Inventor: Akihiko Kawanaka, Hyogo (JP)

(73) Assignees: Daiwabo Holdings Co., Ltd., Osaka (JP); Daiwabo Polytec Co., Ltd., Osaka (JP)

( * ) Notice: Subject to any disclaimer, the term of this patent is extended or adjusted under 35 U.S.C. 154(b) by 345 days.

(21) Appl. No.: 12/995,877

(22) PCT Filed: Jun. 2, 2009

(86) PCT No.: PCT/JP2009/060053
§ 371 (c)(1),
(2), (4) Date: Dec. 23, 2010

(87) PCT Pub. No.: WO2009/148048
PCT Pub. Date: Dec. 10, 2009

(65) Prior Publication Data
US 2011/0081391 A1    Apr. 7, 2011

(30) Foreign Application Priority Data

Jun. 2, 2008 (JP) ................................ 2008-144636

(51) Int. Cl.
| | | |
|---|---|---|
| *A61K 8/02* | (2006.01) | |
| *D04H 1/42* | (2012.01) | |
| *D04H 1/4382* | (2012.01) | |
| *D04H 1/46* | (2012.01) | |
| *A45D 34/00* | (2006.01) | |
| *A61Q 19/00* | (2006.01) | |

(52) U.S. Cl.
CPC .............. *A45D 34/00* (2013.01); *A61K 8/0212* (2013.01); *A61Q 19/00* (2013.01); *D04H 1/42* (2013.01); *D04H 1/4382* (2013.01); *D04H 1/465* (2013.01); *A45D 2200/1027* (2013.01); *A45D 2200/1036* (2013.01); *A61K 2800/75* (2013.01)
USPC ........................................................ 424/401

(58) Field of Classification Search
USPC ......................................................... 424/401
See application file for complete search history.

(56) References Cited

U.S. PATENT DOCUMENTS

2008/0069845 A1* 3/2008 Makihara et al. ............. 424/401

FOREIGN PATENT DOCUMENTS

| JP | 2006-57211 | | 3/2006 | |
|---|---|---|---|---|
| JP | 2006057211 | A * | 3/2006 | .................... 424/401 |
| JP | 2006-110796 | | 4/2006 | |
| JP | 2006-316002 | | 11/2006 | |
| JP | 3944526 | | 7/2007 | |
| WO | WO 2006/016601 A1 | | 2/2006 | |
| WO | WO2006016601 | * | 2/2006 | .................... 424/401 |

OTHER PUBLICATIONS

JP2006057211 A, Aota, published Mar. 2, 2008, machine translation provided.*

* cited by examiner

*Primary Examiner* — Audrea Buckley
(74) *Attorney, Agent, or Firm* — Hamre, Schumann, Mueller & Larson, P.C.

(57) ABSTRACT

A skin-covering sheet for impregnation with a cosmetic preparation according to the present invention includes a non-woven fabric in which a splittable conjugate fiber containing at least two components as viewed in fiber cross-section, namely a polyethylene component and another polymer component, and a hydrophilic fiber are blended, and hydroentangled. The conjugate fiber is partially split and includes a polyethylene ultrafine fiber having a fineness of 0.6 dtex or less. A face mask according to the present invention includes the skin-covering sheet for impregnation with a cosmetic preparation impregnated with 500 to 2000 mass % of a liquid containing a cosmetic preparation. It is therefore possible to obtain a skin-covering sheet for impregnation with a cosmetic preparation and a face mask that have good impregnating ability of a cosmetic liquid into the sheet layer, cause very little irritation to the skin, and are soft in texture.

9 Claims, 2 Drawing Sheets

SKIN-COVERING SHEET FOR IMPREGNATION WITH COSMETIC PREPARATION AND FACE MASK

TECHNICAL FIELD

The present invention relates to a skin-covering sheet for impregnation with a cosmetic preparation and a face mask that are made of a specific non-woven fabric.

BACKGROUND ART

Conventionally, face-covering cosmetic sheets impregnated with cosmetic preparations such as face masks are known. Patent Document 1, for example, proposes a face mask made of a laminated non-woven fabric in which a hydrophilic fiber layer provided as an inner layer and a splittable conjugate fiber layer provided as at least one surface are combined into one and an ultrafine fiber layer serves as a skin contact surface.

Patent Document 2 proposes a water-soluble polymer-containing cosmetic composition for impregnation into a non-woven fabric including a sheath-core type conjugate fiber as a constituent fiber, containing an ethylene-vinyl alcohol copolymer as a sheath component.

PRIOR ART DOCUMENTS

Patent Documents

Patent Document 1: Japanese Patent No. 3944526
Patent Document 2: JP 2006-316002A

SUMMARY OF INVENTION

Problem to be Solved by the Invention

However, the invention of Patent Document 1 is problematic in that the ultrafine fiber layer formed by the hydrophobic splittable conjugate fiber being split is placed on a surface layer, and thus a cosmetic liquid does not easily permeate into the non-woven fabric. Also, Patent Document 2 is considered not preferable because, as disclosed in paragraph [0018], in splittable fibers, ethylene-vinyl alcohol copolymer can exist only on a part of the fiber surface, and therefore biocompatibility based on hydrophilicity, non-water-absorption properties and thermal conductivity cannot be exhibited.

In order to alleviate the problems encountered with the conventional techniques, the present invention provides a skin-covering sheet for impregnation with a cosmetic preparation and a face mask that have good impregnating ability of a cosmetic liquid into the sheet layer, cause very little irritation to the skin, and have a soft texture.

Means for Solving Problem

A skin-covering sheet for impregnation with a cosmetic preparation according to the present invention is a skin-covering sheet for impregnation with a cosmetic preparation including a non-woven fabric in which a splittable conjugate fiber containing at least two components as viewed in fiber cross-section, namely a polyethylene component and another polymer component, and a hydrophilic fiber are blended, and hydroentangled, wherein the conjugate fiber is partially split and includes a polyethylene ultrafine fiber having a fineness of 0.6 dtex or less.

A face mask according to the present invention includes the above-described skin-covering sheet for impregnation with a cosmetic preparation that is impregnated with a liquid containing a cosmetic preparation in an amount of 500 to 2000 mass %.

Effects of the Invention

In the skin-covering sheet for impregnation with a cosmetic preparation and the face mask according to the present invention, a splittable conjugate fiber and a hydrophilic fiber are blended, and therefore the impregnating ability of a cosmetic liquid into the sheet layer is good. Furthermore, the splittable conjugate fiber and the hydrophilic fiber are hydroentangled, and the conjugate fiber is partially split and includes a polyethylene ultrafine fiber having a fineness of 0.6 dtex or less. Thus, the skin-covering sheet for impregnation with a cosmetic preparation and the face mask are very easy to handle, provide a good adhesion to the skin, and cause very little irritation to the skin.

MODES FOR CARRYING OUT THE INVENTION

Figure 1:
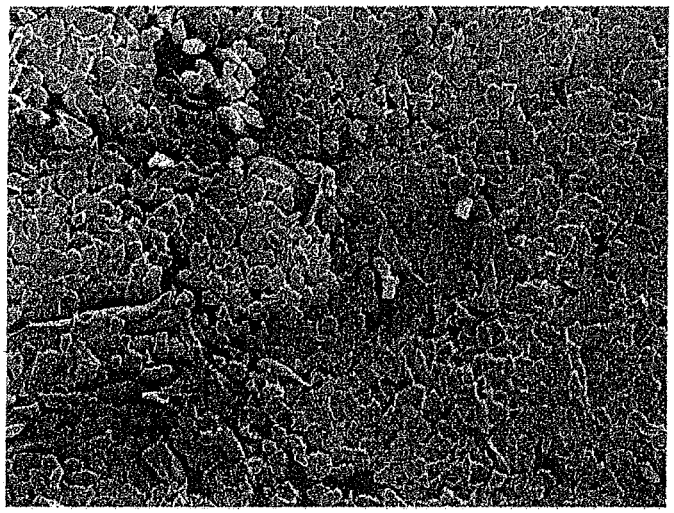
FIG. 1 is an electron micrograph (magnified 300 times) of a non-woven fabric obtained in Example 2 of the present invention.

According to the present invention, a splittable conjugate fiber containing at least two components as viewed in fiber cross-section, namely a polyethylene component and another polymer component, and a hydrophilic fiber are blended. Such a blend is generally used because a uniform blend can be obtained by simultaneously performing opening and blending with an opener (carding machine). Alternatively, the blend can also be obtained by other methods such as wet-laying, air blending and air-laying. The conjugate fiber and the hydrophilic fiber are passed through an opener (carding machine) to form a web (fiber assemblies). Pressurized water is injected to the web so as to hydroentangle the constituent fibers into one mass to obtain a non-woven fabric. Through the hydroentanglement, the conjugate fiber is partially split, and a polyethylene ultrafine fiber having a fineness of 0.6 dtex or less is formed. The monolayer non-woven fabric thus obtained is used as a skin-covering sheet for impregnation with a cosmetic preparation. The reason that the covering sheet of the present invention provides good adhesion to the skin and causes very little irritation to the skin is not clearly known, but is presumably because the polyethylene ultrafine fiber having a fineness of 0.6 dtex or less created by the splittable conjugate fiber being partially split has poor fiber entanglement properties compared to fibers made of other resins, so that appropriate voids can be held easily between fibers, and the polyethylene ultrafine fiber unravels easily when the non-woven fabric is stretched, as a result of which the non-woven fabric can be stretched even with a small force.

Examples of the polyethylene include polymers, such as high-density polyethylene, medium-density polyethylene, low-density polyethylene and linear low-density polyethylene, polymerized with a Ziegler-Natta catalyst, a metallocene catalyst or the like, and copolymers thereof.

The polyethylene ultrafine fiber preferably has a fineness of 0.5 dtex or less, and more preferably 0.3 dtex or less. The lower limit of the fineness of the polyethylene ultrafine fiber is preferably 0.1 dtex or more, and more preferably 0.2 dtex or more. Because the fineness of the polyethylene ultrafine fiber is a factor that influences the softness, adhesion and initial elongation properties (a stress required to elongate the non-woven fabric by 10% from the start of elongation) of the non-woven fabric, with the fineness within the above range, it is possible to obtain a sheet that is soft and easy to stretch during initial elongation.

It is preferable that the splittable conjugate fiber has a cross-sectional fiber structure in which at least one of the constituent components is sectioned into two or more in fiber cross-section, at least a part of the constituent components is exposed at the fiber surface, and the exposed portions are formed continuously in the length direction of the fiber. The splittable conjugate fiber has, for example, a solid or hollow cross section having a circular shape or other shape. The shape in fiber cross-section after being split can be, for example, a radial or layered shape.

There is no particular limitation on the fineness of the splittable conjugate fiber as long as a polyethylene ultrafine fiber having a fineness of 0.6 dtex or less can be obtained, but the fineness of the splittable conjugate fiber is preferably 1 to 9 dtex, and more preferably 1.5 to 4.5 dtex. It is preferable that the number of pieces into which the splittable conjugate fiber is split is, for example, 4 to 32, and more preferably 4 to 20. Particularly when the number of pieces is 6 to 10, the split pieces obtained by radially splitting the splittable conjugate fiber have a substantially triangular cross-sectional shape in fiber cross-section, and therefore appropriate voids can be secured in the non-woven fabric, making the non-woven fabric more likely to stretch during initial elongation. On the other hand, in the case of a splittable conjugate fiber having a layered-shape or a conjugate fiber having a relatively large number of radially split pieces, the polyethylene ultrafine fiber has a fiber cross section close to a flat shape, and therefore it is unlikely to secure voids in the non-woven fabric. When the conjugate fiber is split into a large number of pieces, the degree of entanglement increases, and as a result, voids are unlikely to be secured in the non-woven fabric.

The volume ratio between components (polyethylene and another resin) constituting the splittable conjugate fiber is preferably 2:8 to 8:2. When the volume ratio falls within the above range, the productivity of the conjugate fiber and the splitability of the conjugate fiber are likely to be high. More preferably, the volume ratio between polyethylene and another resin is 4:6 to 6:4.

In the present invention, when the total amount of the conjugate fiber and the fiber obtained from the conjugate fiber being split is taken as 100 mass %, the amount of the polyethylene ultrafine fiber having a fineness of 0.6 dtex or less falls within a range of preferably 10 to 90 mass %, more preferably 10 to 40 mass %, and even more preferably 10 to 30 mass %. The amount within the above range brings about little irritation to the skin. When the amount of the polyethylene ultrafine fiber is less than 10 mass %, the adhesion to the skin becomes insufficient. When the amount of the polyethylene ultrafine fiber exceeds 90 mass %, the fibers are strongly entangled, making the sheet unlikely to stretch.

The "polyethylene ultrafine fiber having a fineness of 0.6 dtex or less" as used herein refers to a fiber that includes at least in part a polyethylene resin component and that has a fineness of 0.6 dtex or less, and it encompasses, for example, a single-component polyethylene ultrafine fiber obtained from the splittable conjugate fiber being completely split into pieces, and a polyethylene ultrafine conjugate fiber obtained from the splittable conjugate fiber being partially split rather than being completely split into pieces, i.e., in which the polyethylene component and one or more other fiber components are attached. The polyethylene ultrafine fiber having a fineness of 0.5 dtex or less can be obtained by adjusting the degree of splitting of the splittable conjugate fiber. The conjugate fiber can be split by, for example, injecting pressurized water at 2 to 10 MPa, more preferably 3 to 8 MPa, from orifices having a pore diameter of 0.05 to 0.3 mm in a hydroentanglement process, whereby it is possible to form the polyethylene ultrafine fiber efficiently.

It is preferable that the polyethylene ultrafine fiber includes a fiber (hereinafter also referred to as "polyethylene ultrafine conjugate fiber") that is paired with and attached to another fiber component. In this case, the polyethylene ultrafine fiber includes a polyethylene ultrafine single fiber and a polyethylene ultrafine conjugate fiber. The polyethylene ultrafine single fiber preferably has a fineness of 0.4 dtex or less, and more preferably 0.3 dtex or less. The lower limit of the fineness of the polyethylene ultrafine single fiber is preferably 0.06 dtex or more, more preferably 0.1 dtex or more, and even more preferably 0.15 dtex or more. The polyethylene ultrafine conjugate fiber preferably has a fineness of 0.6 dtex or less. The lower limit of the fineness of the polyethylene ultrafine conjugate fiber is preferably 0.12 dtex or more, and more preferably 0.2 dtex or more.

It is preferable that the polyethylene ultrafine conjugate fiber is included in the polyethylene ultrafine fiber in an amount of 10 to 30 mass %. This is because when the polyethylene ultrafine conjugate fiber is included, an appropriate thickness and strength can be given to the non-woven fabric.

The split ratio of the splittable conjugate fiber is preferably 20 to 80%, and more preferably 30 to 60%. When the split ratio is less than 20%, for example, the texture is likely to be hard. When the split ratio exceeds 80%, for example, the content of ultrafine fiber having a fineness of 0.6 dtex or less increases, and the non-woven fabric itself becomes dense, as a result of which the initial elongation properties are likely to be high, making it difficult to handle as a skin covering sheet.

As the other component, a resin other than the polyethylene is used, and the other component is preferably at least one selected from polyester, polyolefin, polyamide, polylactic acid, and ethylene-vinyl alcohol copolymer. More preferably, polyester is used. Polyethylene and polyester are separated and split easily by pressurized water. Examples of polyester include aromatic polyesters such as polyethylene terephthalate, polybutylene terephthalate and polytrimethylene terephthalate, aliphatic polyesters such as polylactic acids and polybutylene succinate, and copolymer polyesters such as aromatic-aliphatic polyesters. Polyester is bulky, soft in texture and hydrophobic, and therefore appropriate wettability can be imparted to the non-woven fabric while securing appropriate voids.

In the above-described polyester, it is preferable that an inorganic material such as titanium oxide or zinc oxide is incorporated in an amount of 0.5 to 10 mass % with respect to the resin because the non-woven fabric becomes softer and easier to stretch during initial elongation. More preferably, the inorganic material content is 1 to 8 mass %, and even more preferably 4 to 7 mass %.

It is preferable to use polytrimethylene terephthalate as the polyester because the non-woven fabric becomes softer and easier to stretch during initial elongation. In addition, polytrimethylene terephthalate provides a close fit to the skin because it has a high restoring force.

It is preferable that the blend ratio between the splittable conjugate fiber and the hydrophilic fiber is 30 to 90 mass % for the splittable conjugate fiber and 10 to 70 mass % for the hydrophilic fiber, more preferably 40 to 75 mass % for the conjugate fiber and 25 to 60 mass % for the hydrophilic fiber, and even more preferably 50 to 70 mass % for the conjugate fiber and 30 to 50 mass % for the hydrophilic fiber. The blend ratio within the above range brings about little irritation to the skin, and the residual hydrophilic fiber is blended uniformly, so that good impregnating ability of a cosmetic liquid into the sheet layer is obtained.

In the present invention, the splittable conjugate fiber and the hydrophilic fiber only need to be in a blended state.

There is no particular limitation on the hydrophilic fiber as long as a material having wettability (hydrophilicity) to liquids containing water and cosmetic preparations is used. For example, the hydrophilic fiber is preferably at least one selected from cotton, rayon (including solvent-spun cellulose), pulp (paper), acrylic, and polyester that has undergone a hydrophilic treatment. Among them, cotton, rayon (including solvent-spun cellulose) and pulp (paper) are preferable because they are made of cellulose fibers, and thus can absorb and hold water by themselves, or in other words, they have high absorbency, and are gentle on the skin. Also, the present invention is a monolayer non-woven fabric in which a hydrophilic fiber is blended, and the hydrophilic fiber is exposed at the surface, so that the wettability to liquids (cosmetic preparations) is practically constant, whereas in the case of a laminated non-woven fabric in which a hydrophobic ultrafine fiber is used for a surface layer and a hydrophilic fiber is used for an intermediate layer, because a thin film of a liquid (cosmetic preparation) is formed on the surface, the laminated non-woven fabric provides a good skin feel, but there is a possibility of the liquid evaporating over time. In particular, viscose rayon, cuprammonium rayon (cupra) and solvent-spun cellulose (for example, Lenzing's "Lyocell", "Tencel", etc.) are preferable because they have a uniform fineness and high water-absorbing and swelling properties, and therefore can provide uniform wettability and high softness.

The hydrophilic fiber is preferably a cellulose fiber having a fineness of 0.1 to 4.4 dtex, more preferably 0.3 to 3 dtex, and even more preferably 0.5 to 2 dtex. The cellulose fiber having a fineness within the above range is preferable because the material can exhibit a good hydroentanglement level and can be entangled appropriately with the splittable conjugate fiber and the polyethylene ultrafine fiber, and it is therefore possible to obtain a non-woven fabric that can stretch easily during initial elongation and prevent lint (release of fibers) of the non-woven fabric surface while securing voids. In addition, a soft texture and high water retention also are obtained.

The fineness ratio between the hydrophilic fiber and the polyethylene ultrafine fiber (hydrophilic fiber/polyethylene ultrafine fiber) is preferably 0.3 to 40, more preferably 1 to 15, and even more preferably 2.5 to 8. When the fineness ratio falls within the above range, appropriate voids can be secured in the non-woven fabric, and the non-woven fabric easily is stretched during initial elongation. In addition, when the splittable conjugate fiber and the cellulose fiber are blended in a ratio within the above range, the cellulose fiber absorbs water and swells, and thus the density of the non-woven fabric increases, giving a smooth feel to the skin to the non-woven fabric surface.

It is preferable that the non-woven fabric has a mass per unit area of 30 to 150 g/m$^2$, more preferably 40 to 120 g/m$^2$, and even more preferably 45 to 110 g/m$^2$. The mass per unit area of the non-woven fabric can be adjusted as appropriate according to the amount of liquid impregnated, the adhesion to the skin and the like.

It is preferable that the covering sheet of the present invention has a stress at 10% elongation in the length direction of the sheet in a dry state of 2 to 20 N/5 cm and a stress at 10% elongation in the width direction of the same of 0.1 to 1 N/5 cm, and a stress at 10% elongation in the length direction of the sheet in a wet state of 1 to 15 N/5 cm and a stress at 10% elongation in the width direction of the same of 0.08 to 0.9 N/5 cm. More preferably, the covering sheet in a dry state has a stress at 10% elongation in the length direction of the sheet of 2.5 to 17 N/5 cm and a stress at 10% elongation in the width direction of 0.15 to 0.85 N/5 cm, and even more preferably a stress at 10% elongation in the length direction of 2.5 to 15 N/5 cm and a stress at 10% elongation in the width direction of 0.15 to 0.7 N/5 cm. On the other hand, it is more preferable for the covering sheet in a wet state to have a stress at 10% elongation in the length direction of the sheet of 2 to 13 N/5 cm and a stress at 10% elongation in the width direction of 0.1 to 0.8 N/5 cm, and even more preferably a stress at 10% elongation in the length direction of 2.5 to 10 N/5 cm and a stress at 10% elongation in the width direction of 0.15 to 0.7 N/5 cm. The stress at 10% elongation of the non-woven fabric is used as an indicator for ease of handling of the non-woven fabric, or in other words, it indicates the ease of operation when manually handling the non-woven fabric such as an operation of taking the sheet out of the product package and an operation of fitting the sheet to the skin. When the stress at 10% elongation falls within the above range, the sheet stretches slightly when taking it out of the product package but does not break, resulting in excellent ease of handling. In the case where the skin-covering sheet for impregnation with a cosmetic preparation is used as a face mask, the sheet can be stretched in two directions with a suitable force when attaching it to the skin, and therefore the sheet exhibits a good attachability and an excellent fit (adhesion) to the skin.

The non-woven fabric preferably has a mean flow pore diameter measured in accordance with ASTM F 316 (bubble point method) of 30 to 60 μm, and more preferably 40 to 55 μm. The mean flow pore diameter of the non-woven fabric is an indicator indicating a void diameter determined according to the degree of splitting of the splittable conjugate fiber, the blend ratio between the splittable conjugate fiber and the hydrophilic fiber, the degree of entanglement of fibers, and the like. When the mean flow pore diameter satisfies the above range, appropriate fiber entanglement can be achieved, and a soft texture, a good elongation ability, in particular, initial elongation properties, of the sheet, and good impregnating ability and retention of cosmetic preparations can be obtained.

The non-woven fabric preferably has a smallest detected pore diameter measured in accordance with ASTM F 316 (bubble point method) of 15 μm or more, and more preferably 20 to 35 μm. Similar to the mean flow pore diameter, the smallest detected pore diameter of the non-woven fabric is an indicator indicating a void diameter determined according to the degree of splitting of the splittable conjugate fiber, the blend ratio between the splittable conjugate fiber and the hydrophilic fiber, the degree of entanglement of fibers, and the like. When the smallest detected pore diameter satisfies the above range, liquids (cosmetic preparations) easily can permeate into and out of the sheet, and thus good impregnating ability of liquids (cosmetic preparations) into the sheet and high productivity in the manufacturing process are obtained, and it is likely that the wettability is practically constant. The smallest detected pore diameter takes on a value smaller than the numerical value of the mean flow pore diameter.

EXAMPLES

Hereinafter, the present invention will be described more specifically by way of illustrative examples. It is to be understood that the present invention is not limited to the examples given below.

1. Splittable Conjugate Fiber

The following splittable conjugate fibers were used.

(1) Conjugate fiber A: a splittable conjugate fiber made of high-density polyethylene (PE) and polyethylene terephtalate (PET), radially split into eight pieces and having a fineness of 2.2 dtex and a fiber length of 51 mm (2) Conjugate fiber B: a splittable conjugate fiber made of polypropylene (PP) and high-density polyethylene (PE), radially split into sixteen pieces and having a fineness of 2.2 dtex and a fiber length of 51 mm (3) Conjugate fiber C: a splittable conjugate fiber made of polypropylene (PP) and polyethylene terephtalate (PET), radially split into sixteen pieces and having a fineness of 3.3 dtex and a fiber length of 45 mm (4) Conjugate fiber D: a splittable conjugate fiber made of a polypropylene (PP) and ethylene vinyl alcohol (EVOH), radially split into sixteen pieces and having a fineness of 3.3 dtex and a fiber length of 45 mm (5) Conjugate fiber E: a splittable conjugate fiber made of high-density polyethylene (PE) and polyethylene terephtalate (PET) containing 6 mass % of titanium oxide, radially split into eight pieces and having a fineness of 2.2 dtex and a fiber length of 51 mm (6) Conjugate fiber F: a splittable conjugate fiber made of high-density polyethylene (PE) and polytrimethylene terephtalate (PTT), radially split into eight pieces and having a fineness of 2.2 dtex and a fiber length of 51 mm 2. Hydrophilic Fiber (1) Hydrophilic fiber A: viscose rayon (trade name: "Corona" available from Daiwabo Rayon Co., Ltd., fineness: 1.7 dtex, and fiber length: 40 mm) was used.

(2) Hydrophilic fiber B: viscose rayon (trade name: "Corona" available from Daiwabo Rayon Co., Ltd., fineness: 3.3 dtex, and fiber length: 40 mm) was used.

(3) Hydrophilic fiber C: cotton (trade name: "MSD Cotton" available from Marusan Industry Co., Ltd., average fineness: 2.5 dtex, and average fiber length: 35 mm) was used.

3. Measurement Method of Physical Properties (1) Strength, Stress at 10% Elongation and Elongation These were measured in accordance with JIS-L1096.

(2) Texture

Texture was measured in accordance with Handle-O-Meter method of JIS-L1096.

(3) Liquid Impregnating Ability

Absorption speed was measured by dropping a droplet of water containing a surfactant (0.1% of Family Fresh (available from Kao Corporation)) onto a non-woven fabric surface.

A: Less than one second
B: Not less than one second and less than three seconds
C: Not less than three seconds (4) Fit Sensory evaluation was performed by impregnating a non-woven fabric with water, wringing out the non-woven fabric by hand, and applying the non-woven fabric to the face.

A: Fits closely to the skin even if there is a movement of the skin, exhibiting a good fit B: Not fit to the skin as closely as in the case of A, but there is no practical problem
C: Separates partially from the skin if there is a movement of the skin, exhibiting a poor fit
D: Separates largely from the skin if there is a movement of the skin (5) Skin Irritation Sensory evaluation for skin irritation was performed at the same time the fit test was carried out.

A: No skin irritation was observed
B: Slight skin irritation was observed
C: Obvious skin irritation was observed (6) Split Ratio Split ratio was determined in the following manner A non-woven fabric was bundled so as to not create a space, and then cut. The cross section of the bundled non-woven fabric was imaged with an electron microscope at a magnification of 300 times, and the number of conjugate fibers and fibers into which the conjugate fibers were split was counted in the field of view. The split ratio was calculated by the following equation.

Split ratio(%)=[Number of fibers with fineness of 0.5 dtex or less/Number of conjugate fibers and fibers obtained from conjugate fibers being split]×100

(7) Pore Diameter Distribution

Smallest detected pore diameter, bubble point pore diameter and mean flow pore diameter were measured by using "Palm Porometer" available from Porous Materials Inc. in accordance with ASTM F 316-86 (bubble point method).

Examples 1 to 5

Figure 2:
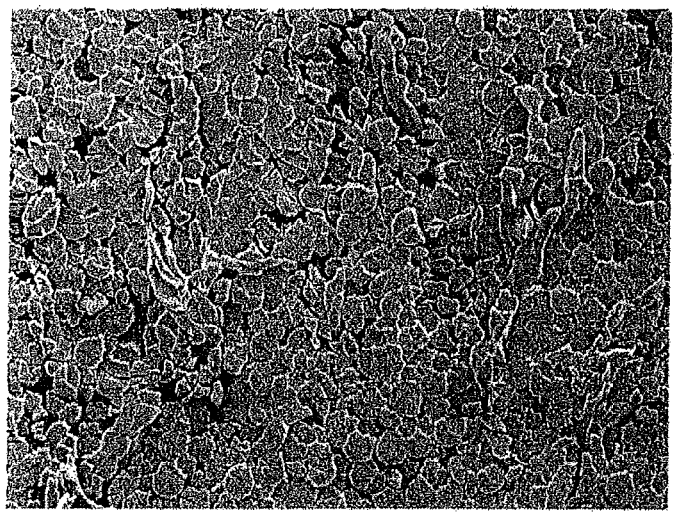
FIG. 2 is an electron micrograph (magnified 300 times) of a non-woven fabric obtained in Example 3 of the present invention.

A splittable type conjugate fiber(s) and a hydrophilic fiber shown in Table 1 were opened and blended by a carding machine to produce a parallel carded web. Next, a columnar water stream was injected to the front side of the carded web at water pressures of 2 MPa and 3 MPa (injected to the front side twice in total) and to the back side of the carded web at a water pressure of 3 MPa from a nozzle provided with orifices having a pore diameter of 0.1 mm at a pitch of 0.6 mm, so as to entangle constituent fibers and to partially split the conjugate fiber. The obtained non-woven fabric had a mass per unit area of 70 g/m$^2$. The conditions and results are shown collectively in Table 1. A cross sectional micrograph of the non-woven fabric of Example 2 in a bundled state is shown in FIG. 1, and a cross sectional micrograph of the non-woven fabric of Example 3 in a bundled state is shown in FIG. 2. The non-woven fabrics of Examples 1 to 5 contained a wedge-shaped single-component polyethylene ultrafine fiber having a fineness of 0.6 dtex or less and a polyethylene ultrafine conjugate fiber in which a polyethylene component and another fiber component were attached. The content of the polyethylene ultrafine fiber can be calculated from the content and split ratio of the splittable conjugate fiber.

Examples 6 and 7

Figure 4:
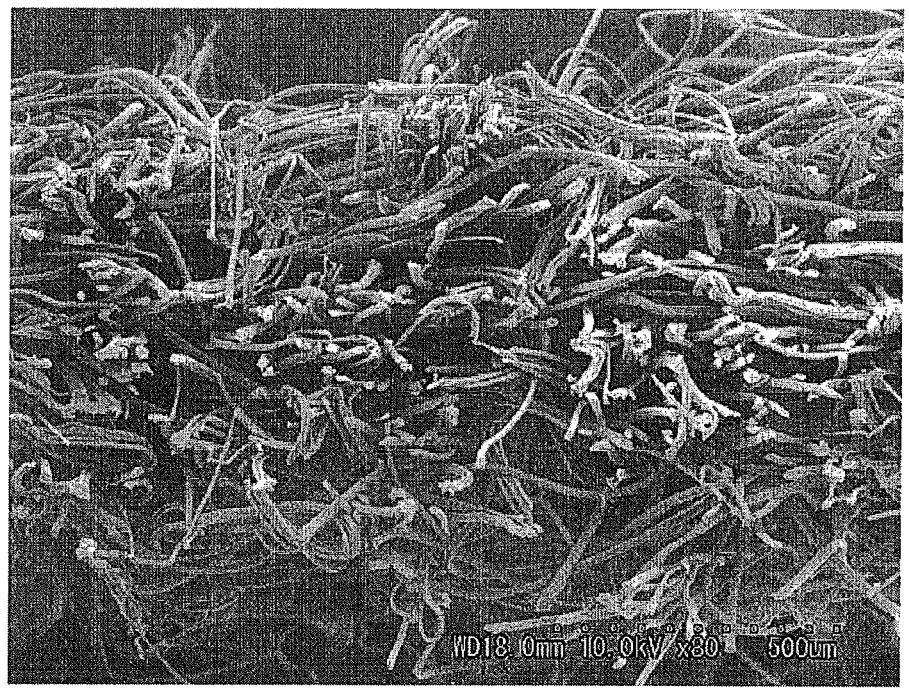
FIG. 4 is an electron micrograph (magnified 80 times) of a non-woven fabric obtained in Example 6 of the present invention.
Figure 5:
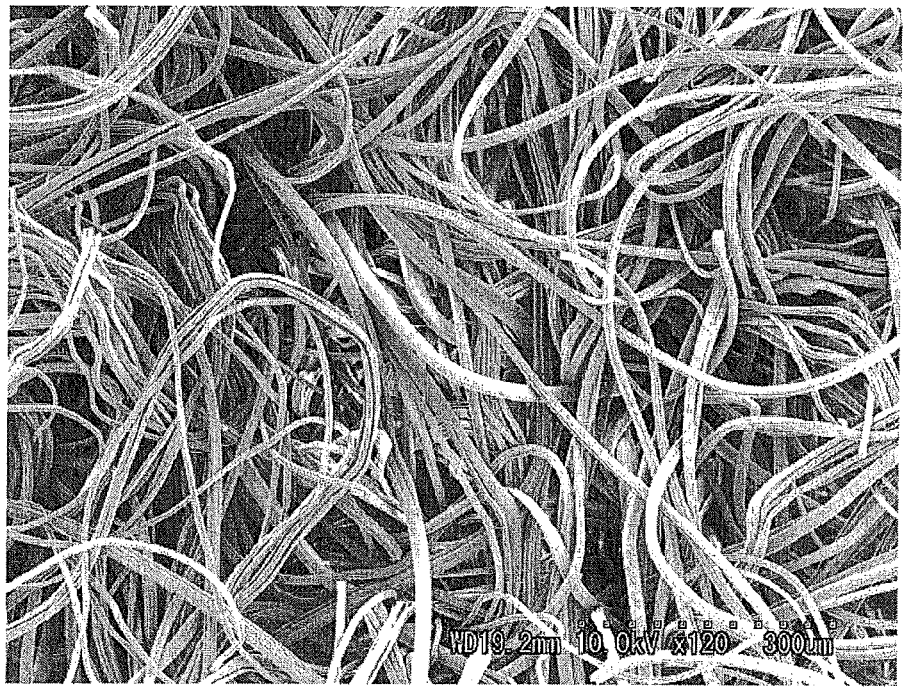
FIG. 5 is an electron micrograph (magnified 120 times) of a non-woven fabric obtained in Example 7 of the present invention.

A splittable type conjugate fiber and a hydrophilic fiber shown in Table 1 were opened and blended by a carding machine to produce a semi-random carded web. Next, a columnar water stream was injected to the front side of the carded web at water pressures of 4 MPa and 6 MPa (injected to the front side twice in total) and to the back side of the carded web at a water pressure of 4 MPa from a nozzle provided with orifices having a pore diameter of 0.1 mm at a pitch of 0.6 mm, so as to entangle constituent fibers and to partially split the conjugate fiber. The conditions and results are shown collectively in Table 1. The non-woven fabrics of Examples 6 and 7 contained a wedge-shaped single-component polyethylene ultrafine fiber having a fineness of 0.6 dtex or less and a polyethylene ultrafine conjugate fiber in which a polyethylene component and another fiber component were attached. A cross sectional micrograph of the non-woven fabric of Example 6 is shown in FIG. 4, and a surface micrograph of the non-woven fabric of Example 7 is shown in FIG. 5.

Example 8

A splittable type conjugate fiber and a hydrophilic fiber shown in Table 1 were opened and blended by a carding machine to produce a semi-random carded web. Next, a columnar water stream was injected to the front side of the carded web at water pressures of 4 MPa and 8 MPa (injected to the front side twice in total) and to the back side of the carded web at a water pressure of 8 MPa from a nozzle-provided with orifices having a pore diameter of 0.1 mm at a pitch of 0.6 mm, so as to entangle constituent fibers and to partially split the conjugate fiber. The conditions and results are shown collectively in Table 1. The non-woven fabric of Example 8 contained a wedge-shaped single-component polyethylene ultrafine fiber having a fineness of 0.6 dtex or less and a polyethylene ultrafine conjugate fiber in which a polyethylene component and another fiber component were attached.

TABLE 1

|  |  | Ex. 1 | Ex. 2 | Ex. 3 | Ex. 4 | Ex. 5 | Ex. 6 | Ex. 7 | Ex. 8 |
|---|---|---|---|---|---|---|---|---|---|
| Constituent fiber mass (%) | Constituent fiber A | 80 | 60 |  | 30 |  | 60 | 60 | 60 |
|  | Constituent fiber B |  |  | 60 | 30 | 60 |  |  |  |
|  | Constituent fiber C |  |  |  |  |  |  |  |  |
|  | Constituent fiber D |  |  |  |  | 20 |  |  |  |
|  | Constituent fiber E |  |  |  |  |  |  |  |  |
|  | Constituent fiber F |  |  |  |  |  |  |  |  |
|  | Hydrophilic fiber A | 20 | 40 | 40 | 40 | 20 | 40 | 40 | 40 |
|  | Hydrophilic fiber B |  |  |  |  |  |  |  |  |
|  | Hydrophilic fiber C |  |  |  |  |  |  |  |  |
|  |  | Blend | Blend | Blend | Blend | Blend | Blend | Blend | Blend |
| Mass per unit area (g/m$^2$) |  | 70 | 70 | 70 | 70 | 70 | 70 | 50 | 100 |
| Split ratio (%) |  | 60 | 70 | 50 | 45 | 65 | 70 | 75 | 70 |
| Dry state | Strength in length direction (N/5 cm) | 155 | 134 | 210 | 172 | 158 | 80 | 52 | 127 |
|  | Strength in width direction (N/5 cm) | 19 | 17 | 15 | 15 | 15 | 35 | 20 | 49 |
|  | Stress at 10% elongation in length direction (N/5 cm) | 4.28 | 5.82 | 9.07 | 7.45 | 7.83 | 3.63 | 3.09 | 15.5 |
|  | Stress at 10% elongation in width direction (N/5 cm) | 0.42 | 0.43 | 0.53 | 0.50 | 0.47 | 0.30 | 0.20 | 0.63 |
|  | Elongation in length direction (%) | 71 | 55 | 45 | 50 | 48 | 82 | 76 | 69 |
|  | Elongation in width direction (%) | 212 | 165 | 173 | 161 | 162 | 169 | 169 | 172 |
| Wet state | Strength in length direction (N/5 cm) | 151 | 137 | 132 | 138 | 118 | 80 | 62 | 117 |
|  | Strength in width direction (N/5 cm) | 4 | 16 | 11 | 14 | 14 | 30 | 22 | 47 |
|  | Stress at 10% elongation in length direction (N/5 cm) | 4.31 | 3.54 | 5.31 | 3.82 | 2.64 | 4.10 | 3.50 | 9.50 |
|  | Stress at 10% elongation in width direction (N/5 cm) | 0.34 | 0.40 | 0.41 | 0.40 | 0.36 | 0.29 | 0.16 | 0.55 |
|  | Elongation in length direction (%) | 67 | 66 | 46 | 55 | 83 | 67 | 69 | 72 |
|  | Elongation in width direction (%) | 172 | 144 | 141 | 146 | 201 | 132 | 69 | 72 |
| Flexural rigidity (g) |  | 29 | 25 | 34 | 33 | 39 | 38 | 26 | 70 |
| Liquid impregnating ability |  | B | A | B | B | B | A | A | A |
| Fit |  | B | A | B | B | B | A | A | A |
| Skin irritation |  | A | A | A | A | A | A | A | A |
| Pore Diameter Distribution | Smallest detected pore diameter (μm) | 23 | 33 | 25 | 19 | 28 | 26 | 28 | 16 |
|  | Bubble point pore diameter (μm) | 97 | 102 | 85 | 99 | 83 | 90 | 123 | 71 |
|  | Mean flow pore diameter (μm) | 54 | 56 | 39 | 45 | 42 | 48 | 53 | 31 |

Examples 9 to 12

Non-woven fabrics were obtained in the same manner as in Example 1, except that a splittable type conjugate fiber and a hydrophilic fiber shown in Table 2 were blended. The non-woven fabrics of Examples 9 to 12 contained a wedge-shaped single-component polyethylene ultrafine fiber having a fineness of 0.6 dtex or less and a polyethylene ultrafine conjugate fiber in which a polyethylene component and another fiber component were attached.

The non-woven fabrics of Examples 1 to 12 were impregnated with a commercially available cosmetic milky lotion in an amount of 700 mass % with respect to the mass of the non-woven fabric. As a result, they exhibited good impregnating ability of the cosmetic liquid into the sheet layer and therefore it was confirmed that they are suitable as skin-covering sheets for impregnation with a cosmetic preparation. Also, the obtained covering sheets were punched into face masks. As a result, it was confirmed that they exhibited ease of handling, good adhesion to the skin and very little irritation to the skin.

Comparative Examples 1 to 4

Figure 3:
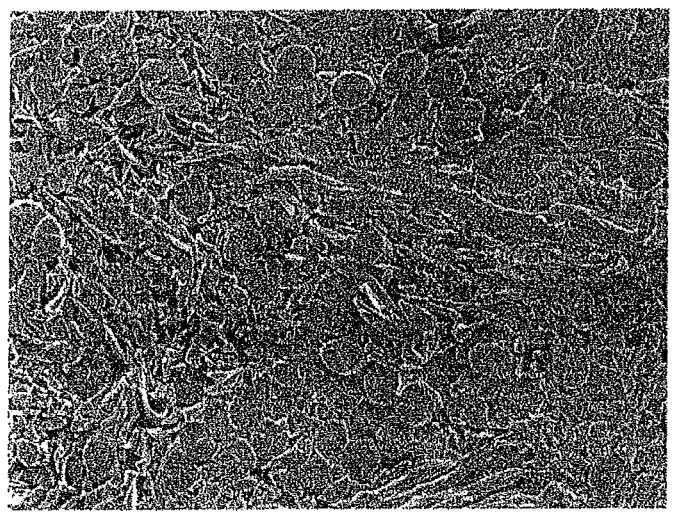
FIG. 3 is an electron micrograph (magnified 300 times) of a non-woven fabric obtained in Comparative Example 1.

Comparative Examples 1 to 4 are different from Examples 1 to 5 in that DF-1 (wedge-shaped splittable fiber made of PP and PET and split into sixteen pieces) was used in Comparative Example 1, a laminated non-woven fabric was produced in Comparative Example 2, and polyethylene was not included as a fiber component constituting a conjugate fiber in Comparative Examples 3 and 4. The conditions and results are shown collectively in Table 2. A cross sectional micrograph of the non-woven fabric of Comparative Example 1 in a bundled state is shown in FIG. 3.

TABLE 2

| | | Ex. 9 | Ex. 10 | Ex. 11 | Ex. 12 | Com. Ex. 1 | Com. Ex. 2 | Com. Ex. 3 | Com. Ex. 4 |
|---|---|---|---|---|---|---|---|---|---|
| Constituent fiber mass (%) | Constituent fiber A | | | 60 | 60 | | 70 | | |
| | Constituent fiber B | | | | | | | | |
| | Constituent fiber C | | | | | 100 | | 60 | |
| | Constituent fiber D | | | | | | | | 60 |
| | Constituent fiber E | 70 | | | | | | | |
| | Constituent fiber F | | 70 | | | | | | |
| | Hydrophilic fiber A | 30 | 30 | | | | 30 | 40 | 40 |
| | Hydrophilic fiber B | | | 40 | | | | | |
| | Hydrophilic fiber C | | | | 40 | | | | |
| | | Blend | Blend | Blend | Blend | Single component | Laminate | Blend | Blend |
| Mass per unit area (g/m²) | | 70 | 70 | 70 | 70 | | | | |
| Split ratio (%) | | 75 | 70 | 70 | 70 | 20 | 60 | 50 | 95 |
| Dry state | Strength in length direction (N/5 cm) | 135 | 140 | 128 | 178 | 83 | 67 | 145 | 210 |
| | Strength in width direction (N/5 cm) | 15 | 18 | 16 | 23 | 11 | 34 | 22 | 32 |
| | Stress at 10% elongation in length direction (N/5 cm) | 4.78 | 4.98 | 5.32 | 8.51 | 1.65 | 3.4 | 10.11 | 22.45 |
| | Stress at 10% elongation in width direction (N/5 cm) | 0.40 | 0.45 | 0.42 | 0.55 | 0.42 | 0.56 | 1.09 | 1.72 |
| | Elongation in length direction (%) | 61 | 63 | 61 | 45 | 66 | 76 | 42 | 38 |
| | Elongation in width direction (%) | 172 | 163 | 170 | 153 | 163 | 148 | 110 | 106 |
| Wet state | Strength in length direction (N/5 cm) | 130 | 135 | 127 | 188 | — | 62 | — | — |
| | Strength in width direction (N/5 cm) | 14 | 17 | 15 | 25 | — | 29 | — | — |
| | Stress at 10% elongation in length direction (N/5 cm) | 4.28 | 4.81 | 4.39 | 8.67 | — | 3.20 | — | — |
| | Stress at 10% elongation in width direction (N/5 cm) | 0.36 | 0.41 | 0.39 | 0.55 | — | 0.64 | — | — |
| | Elongation in length direction (%) | 64 | 67 | 65 | 65 | — | 80 | — | — |
| | Elongation in width direction (%) | 152 | 140 | 157 | 157 | — | 121 | — | — |
| Flexural rigidity (g) | | — | — | — | — | 33 | 25 | 45 | 36 |
| Liquid impregnating ability | | A | A | B | B | B | B | B | B |
| Fit | | A | A | B | B | D | B | C | C |
| Skin irritation | | A | A | B | B | A | A | A | B |
| Pore Diameter Distribution | Smallest detected pore diameter (μm) | — | — | — | — | 11 | 14 | — | — |
| | Bubble point pore diameter (μm) | — | — | — | — | 77 | 96 | — | — |
| | Mean flow pore diameter (μm) | — | — | — | — | 21 | 44 | — | — |

The non-woven fabrics of Examples 1 to 12 contained a polyethylene ultrafine fiber and had an appropriate split ratio and entanglement level, and therefore they exhibited a low stress at 10% elongation, good attachment to the skin, a good fit and little skin irritation. The non-woven fabrics of Examples 1, 2, 6, 7, 9 and 10 had a lower stress at 10% elongation than the other examples, and thus they exhibited good performances particularly in term of attachability, fit and skin irritation. The non-woven fabrics of Examples 9 and 10 were good because they exhibited high softness and a small skin irritation. When Examples 6, 11 and 12 are compared, the non-woven fabric of Example 6 was softer than those of Examples 11 and 12 because a rayon fiber having a fineness of 2 dtex or less was used.

On the other hand, the non-woven fabric of Comparative Example 1 was low in terms of strength and stress at 10% elongation because the split ratio and entanglement level due to hydroentanglement were lower than those of the examples of the present invention, and thus is not suitable for practical application. The non-woven fabric of Comparative Example 3 was made by adding a rayon fiber to the splittable conjugate fiber used in Comparative Example 1, and for this reason the entanglement level increased, and the non-woven fabric strength and the stress at 10% elongation became too high, resulting in poor performances in terms of fit and skin irritation. The non-woven fabric of Comparative Example 4 exhibited a poor fit because the split ratio of the splittable conjugate fiber was high, which facilitated the entanglement of fibers, resulting in an excessively high stress at 10% elongation.

The non-woven fabrics of Examples 1 to 8 had appropriate void diameters as shown in the Pore Diameter Distribution section, and thus they exhibited good performances in terms of liquid impregnating ability, fit and skin irritation. The non-woven fabrics of Examples 1, 2, 6, 7 and 8 were particularly good because the mean flow pore diameter and the smallest detected pore diameter satisfied the predetermined ranges.

INDUSTRIAL APPLICABILITY

The skin-covering sheet for impregnation with a cosmetic preparation of the present invention can be used as a face mask that covers the entire face or that partially covers the face such as the eyes and the mouth, or as a patch that partially covers the body such as the hands, the neck, the elbows, the feet and the abdomen.

The invention claimed is:

1. A sheet for a face mask impregnated with a cosmetic preparation, comprising a non-woven fabric, which is formed of a hydroentangled mass of a splittable conjugate fiber and a hydrophilic fiber that are blended uniformly,
   wherein the splittable conjugate fiber comprises at least two components as viewed in fiber cross-section, which are a polyethylene component and a polymer component other than the polyethylene component,
   the splittable conjugate fiber is included in an amount ranging from 50 to 70 mass %, and the hydrophilic fiber is included in an amount ranging from 30 to 50 mass %,
   the conjugate fiber is partially split and includes a polyethylene ultrafine fiber having a fineness of 0.6 dtex or less,
   the polyethylene ultrafine fiber having a fineness of 0.6 dtex or less is included in an amount ranging from 10 to 40 mass % relative to a total amount of the conjugate fiber and a fiber obtained by splitting the conjugate fiber as 100 mass %,
   the hydrophilic fiber is a cellulose fiber having a fineness of 0.5 to 2 dtex, and the fineness ratio of the hydrophilic fiber relative to the polyethylene ultrafine fiber (hydrophilic fiber/polyethylene ultrafine fiber) is 2.5 to 8,
   a non-woven component layer of the sheet consists essentially of the non-woven fabric, which has a monolayer structure, and
   the non-woven fabric has a smallest detected pore diameter of 15 μm or more, when measured in accordance with ASTM F 316 (bubble point method).

2. The sheet for a face mask impregnated with a cosmetic preparation according to claim 1,
   wherein the polyethylene ultrafine fiber has a fineness of 0.5 dtex or less.

3. The sheet for a face mask impregnated with a cosmetic preparation according to claim 1,
   wherein the polyethylene ultrafine fiber includes a conjugate fiber in which the polyethylene component and one or more other fiber components are attached.

4. The sheet for a face mask impregnated with a cosmetic preparation according to claim 1,
   wherein the other component is polyester.

5. The sheet for a face mask impregnated with a cosmetic preparation according to claim 1,
   wherein the non-woven fabric has a mean flow pore diameter ranging from 30 to 60 μm, when measured in accordance with the ASTM F 316 (bubble point method).

6. A face mask comprising the sheet for a face mask impregnated with a cosmetic preparation according to claim 1, that is impregnated with 500 to 2000 mass % of a liquid containing a cosmetic preparation.

7. The sheet for a mask impregnated with a cosmetic preparation according to claim 4,
   wherein the polyester contains titanium oxide or zinc oxide, or the polyester is polytrimethylene terephthalate.

8. The sheet for a face mask impregnated with a cosmetic preparation according to claim 1,
   wherein the non-woven fabric has a stress of 2 to 20 N/5 cm in a length direction of the sheet at 10% elongation in a dry state and a stress of 0.1 to 1 N/5 cm in a width direction thereof at 10% elongation in a dry state, and a stress of 1 to 15 N/5 cm in the length direction of the sheet at 10% elongation in a wet state and a stress of 0.08 to 0.9 N/5 cm in the width direction thereof at 10% elongation in a wet state.

9. The sheet for a face mask impregnated with a cosmetic preparation according to claim 1,
   wherein the non-woven fabric has the smallest detected pore diameter in a range of 15-35 μm when measured in accordance with ASTM F 316 (bubble point method).

* * * * *